United States Patent
Senibi et al.

(10) Patent No.: US 7,817,843 B2
(45) Date of Patent: *Oct. 19, 2010

(54) MANUFACTURING PROCESS OR IN SERVICE DEFECTS ACOUSTIC IMAGING USING SENSOR ARRAY

(75) Inventors: Simon D Senibi, Covington, WA (US); David L Banks, Bellevue, WA (US); Chris K Carrell, Bothell, WA (US); Mark A Curry, Lynwood, WA (US)

(73) Assignee: The Boeing Company, Chicago, IL (US)

( * ) Notice: Subject to any disclaimer, the term of this patent is extended or adjusted under 35 U.S.C. 154(b) by 976 days.

This patent is subject to a terminal disclaimer.

(21) Appl. No.: 10/793,504

(22) Filed: Mar. 4, 2004

(65) Prior Publication Data

US 2005/0209791 A1 Sep. 22, 2005

(51) Int. Cl.
*G06K 9/00* (2006.01)
(52) U.S. Cl. ..................................... 382/141
(58) Field of Classification Search ................. 382/141
See application file for complete search history.

(56) References Cited

U.S. PATENT DOCUMENTS

| | | | | |
|---|---|---|---|---|
| 3,672,210 | A * | 6/1972 | Cressman et al. | 73/612 |
| 4,180,790 | A * | 12/1979 | Thomas | 367/7 |
| 4,265,120 | A | 5/1981 | Morris et al. | |
| 4,265,124 | A | 5/1981 | Lim et al. | |
| 4,546,652 | A | 10/1985 | Virkar et al. | |
| 4,567,769 | A | 2/1986 | Barkhoudarian | |
| 4,856,335 | A * | 8/1989 | Tornberg | 73/597 |
| 4,895,072 | A * | 1/1990 | Rich et al. | 101/376 |
| 5,142,141 | A | 8/1992 | Talat et al. | |
| 5,227,731 | A | 7/1993 | Prabhakaran et al. | |
| 5,329,930 | A | 7/1994 | Thomas, III et al. | |
| 5,625,150 | A * | 4/1997 | Greene et al. | 73/649 |
| 5,814,729 | A * | 9/1998 | Wu et al. | 73/588 |
| 5,891,038 | A * | 4/1999 | Seyed-Bolorforosh et al. | 600/447 |
| 5,897,501 | A * | 4/1999 | Wildes et al. | 600/447 |

(Continued)

FOREIGN PATENT DOCUMENTS

EP    0 952 446 A    10/1999

(Continued)

OTHER PUBLICATIONS

"Ultrasonic Lamb wave tomography", Institute of Physics Publishing, Inverse Problems 18, 2002, 1795-1808, Leonard et al.*

(Continued)

*Primary Examiner*—Bhavesh M Mehta
*Assistant Examiner*—David P Rashid
(74) *Attorney, Agent, or Firm*—Harness, Dickey & Pierce, P.L.C.

(57) ABSTRACT

A mobile platform is provided which has at least one component having an array of distributed piezoelectric transmitters and an associated array of distributed receivers. The receivers are configured to receive ultrasonic transmissions from the transmitters. Data from the receivers is stored in memory and processed through an algebraic reconstruction tomography algorithm which forms an image of the defect within the component. An algorithm is used to determine the position and size of the defect.

19 Claims, 9 Drawing Sheets

FIG. 1

U.S. PATENT DOCUMENTS

| | | | |
|---|---|---|---|
| 5,969,260 A | 10/1999 | Belk et al. | |
| 6,048,315 A | 4/2000 | Chiao et al. | |
| 6,161,434 A * | 12/2000 | Fink et al. | 73/587 |
| 6,182,512 B1 * | 2/2001 | Lorraine | 73/655 |
| 6,236,862 B1 * | 5/2001 | Erten et al. | 455/501 |
| 6,370,964 B1 * | 4/2002 | Chang et al. | 73/862.046 |
| 6,385,474 B1 * | 5/2002 | Rather et al. | 600/407 |
| 6,396,262 B2 * | 5/2002 | Light et al. | 324/240 |
| 6,467,352 B2 * | 10/2002 | Schafer et al. | 73/597 |
| 6,495,833 B1 * | 12/2002 | Alfano et al. | 250/341.8 |
| 6,585,647 B1 * | 7/2003 | Winder | 600/437 |
| 6,792,808 B1 | 9/2004 | Batzinger et al. | |
| 2002/0043108 A1 * | 4/2002 | Schafer et al. | 73/632 |
| 2003/0198381 A1 * | 10/2003 | Tanaka et al. | 382/166 |
| 2003/0219191 A1 * | 11/2003 | Kehlenbach | 385/12 |
| 2003/0220556 A1 * | 11/2003 | Porat et al. | 600/407 |
| 2005/0075846 A1 * | 4/2005 | Kim | 703/1 |

FOREIGN PATENT DOCUMENTS

| | | |
|---|---|---|
| EP | 1 398 627 A | 3/2004 |
| JP | 11 218486 | 8/1999 |

OTHER PUBLICATIONS

"Fan beam and double crosshole Lamb wave tomography for mapping flaws in aging aircraft structures", J. Acoustic Society of America, Oct. 2000, pp. 1631-1639, Malyarenko et al.*

"Parallel projection and crosshole Lamb wave contact scanning tomography", J. Acoustic Society of America, Nov. 1999, pp. 2568-2577, McKeon et al.*

"Damage detection in composite materials using Lamb wave methods", Smart Materials and Structures, 2002, pp. 269-278, Kessler et al.*

* cited by examiner

MANUFACTURING PROCESS OR IN SERVICE DEFECTS ACOUSTIC IMAGING USING SENSOR ARRAY

FIELD OF THE INVENTION

The present invention relates to a system and method of evaluating the structural integrity of components and, more particularly, to a system and method for evaluating structural integrity of components associated with a mobile platform.

BACKGROUND OF THE INVENTION

Current methods for nondestructive analysis of components is labor intensive and time consuming. This is particularly true of composite components in a complex assembled structure such as an aircraft. Nondestructive inspection systems such as through transmission NDI require a structure to be dismantled and moved to the location of an NDI machine. These systems require that the component be submerged in a coupling medium such as water which acts as a sound transmission medium.

While the systems have proven effective in determining the presence of a defect, analysis of transmitted ultrasonic data is difficult and does not readily give the location or defect size information. Further, the disassembly and reassembly of the components is time consuming and expensive.

SUMMARY OF THE INVENTION

The preferred component diagnostic system of the present invention has an array of distributed piezoelectric transceivers coupled to a component. The system uses transmissions from individual transceivers and associated received data from a plurality of receiver sensors to construct an image of a defect within the component.

In one embodiment to the invention, the system utilizes an algebraic reconstruction tomography algorithm to construct an image of the defect. The image is then used to compare the defect with predicted physical properties of the component stored in a database, to determine the health of the component. The health of a component relates to current as well as predicted strength of the component.

In another embodiment, a mobile platform is provided which has at least one component having an array of distributed piezoelectric transmitters and an associated array of distributed receivers. The receivers are configured to receive ultrasonic transmissions from the transmitters. Data from the receivers is stored in memory and processed through an algebraic reconstruction tomography algorithm which forms an image of the defect within the component. An algorithm is used to determine the position and size of the defect.

In another embodiment to the invention, a mobile platform has a plurality of components, each having an array of distributed transceivers. Each individual transceiver within an array is configured to, in succession, alternately produce a broad band pulse which is received by the non-transmitting transceivers. The received signals are then accumulated within a storage device associated with a computer. An algebraic reconstruction tomography algorithm transforms the received signals into defect image and location information.

In another embodiment to the invention, a method is disclosed to determine the location of a defect within an uncured composite component. The method includes coupling a plurality of piezoelectric transceivers to the non-cured composite structure. The system then sets a counter to initial condition for the counter less than the number of transceivers, and performs the following for a number of transceivers: transmitting an ultrasonic signal from one of the transceivers, receiving a response signal from the remaining transceivers, and storing the received information in a memory location, and incrementing the counter. The system then utilizes an algebraic reconstruction tomography algorithm to determine the location of the defect in the uncured composite structure.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
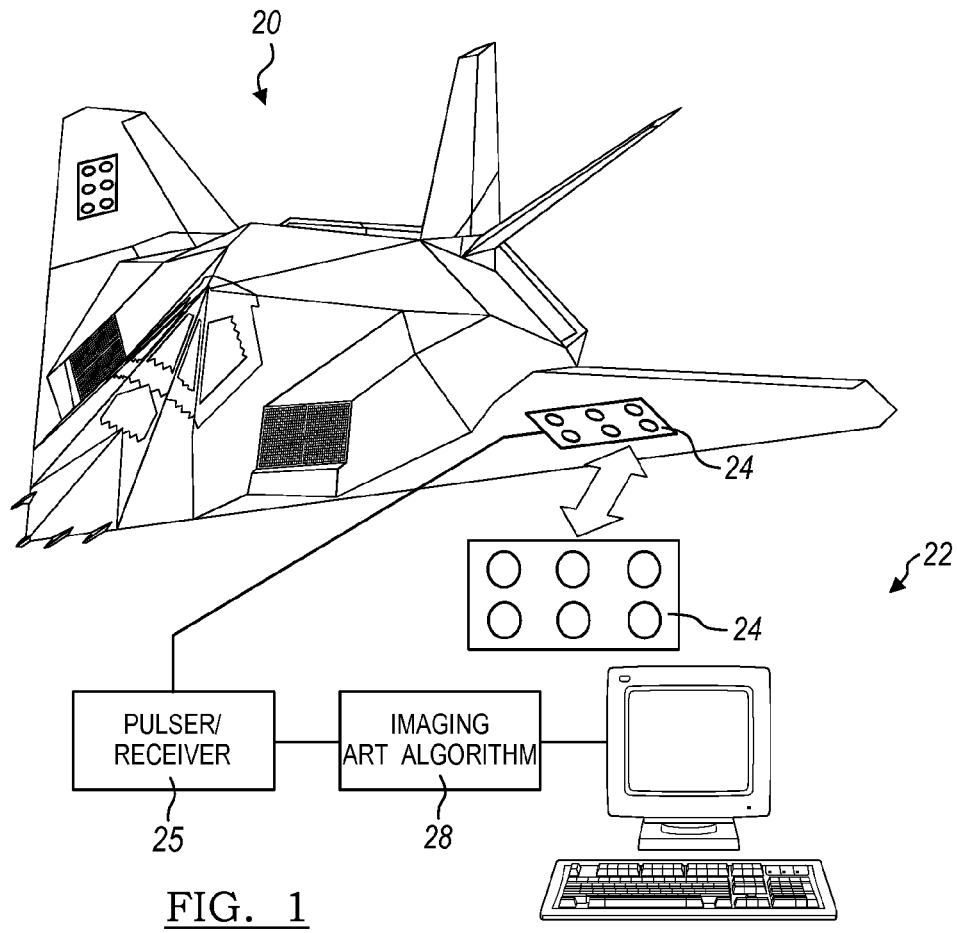
FIG. 1 represents a mobile platform utilizing the defect detection system according to the teachings of the present invention.

FIG. 1 represents a mobile platform 20 utilizing the component evaluation system 22 according to the teachings of the present invention. The component evaluation system 22 is configured to evaluate the health status of a composite component 24 associated with the mobile platform 20. The evaluation system 22 has an array of distributed transmitters and receivers. Coupled to the transmitters and receivers is a circuit 25 which actuates each of the transmitters in succession. The receivers are configured to record the transmission of ultrasonic data through the component 24.

The evaluation system 22 uses an algebraic reconstruction tomography algorithm (ART) 28 to calculate and evaluate velocity information between the transmitters and the sensors. As explained below, the velocity information is used to calculate an image 30 of a defect or defects 31 within the component 24. The image 30 of the defect 31 is then used to evaluate the health of the component and the mobile platform 20.

Figure 2A:
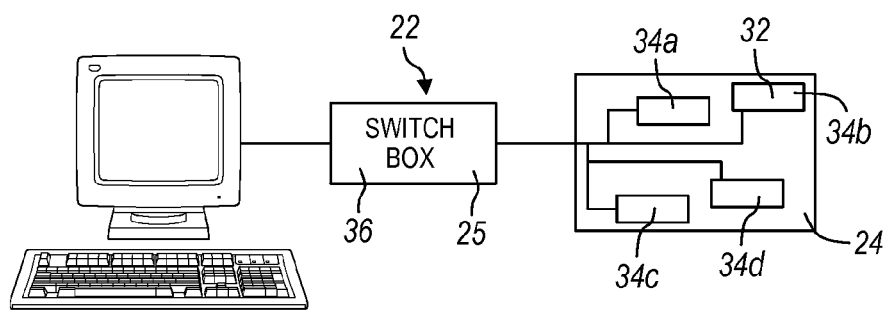
FIG. 2A represents a system showing FIG. 1 configured to evaluate the structural integrity of the component shown in FIG. 1.
Figure 2B:
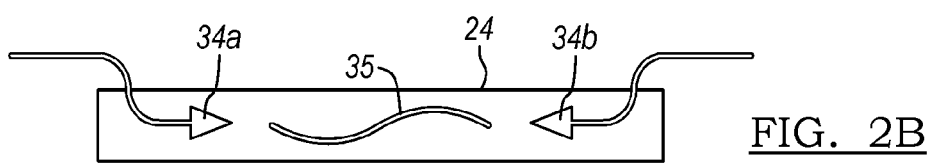
FIG. 2B shows the propagation of Lamb wave 35 through the structure.

As shown in FIGS. 2A and 2B, an array of transmitters and receivers take the form of an array 32 of piezoelectric transceivers 34a-34d. The piezoelectric transceivers 34a-34d are either embedded within the component 24 or distributed over a surface of the component 24. While the array of transceivers are shown evenly distributed, it is envisioned that the spacing between the elements can vary. The piezoelectric transceivers 34 are configured to transmit space and receive broad band ultrasonic vibrations at frequencies from about 200 kHz to about 500 kHz. These piezoelectric transceivers 34 are preferably piezoelectric sensors in distributed array format from Acellent Technologies Inc.

The piezoelectric transceivers shown in FIG. 2B are non-resonant wide band devices which produce a Lamb wave 35 within a component 24 through producing surface "pinching". The Lamb wave 35 produce transmittable in-plane strains within the component 24 which propagate through the length and thickness of the component 24.

The system 22 uses a computer program to control a switching box 36 and to produce data corresponding to physical properties of the defect. Specifically, the data can be an image 30. The switch box 36 regulates which transceiver 34a through 34h will be used to transmit the ultrasonic signal and which transceivers are configured to receive the transmitted signals. Additionally, the switch box 36 additionally is configured to couple analog to digital monitoring hardware to the appropriate transceivers. The monitoring hardware takes the received signal information and stores it within a memory device associated with a computer for later processing by the algebraic reconstruction tomography algorithm 28.

Figure 3:
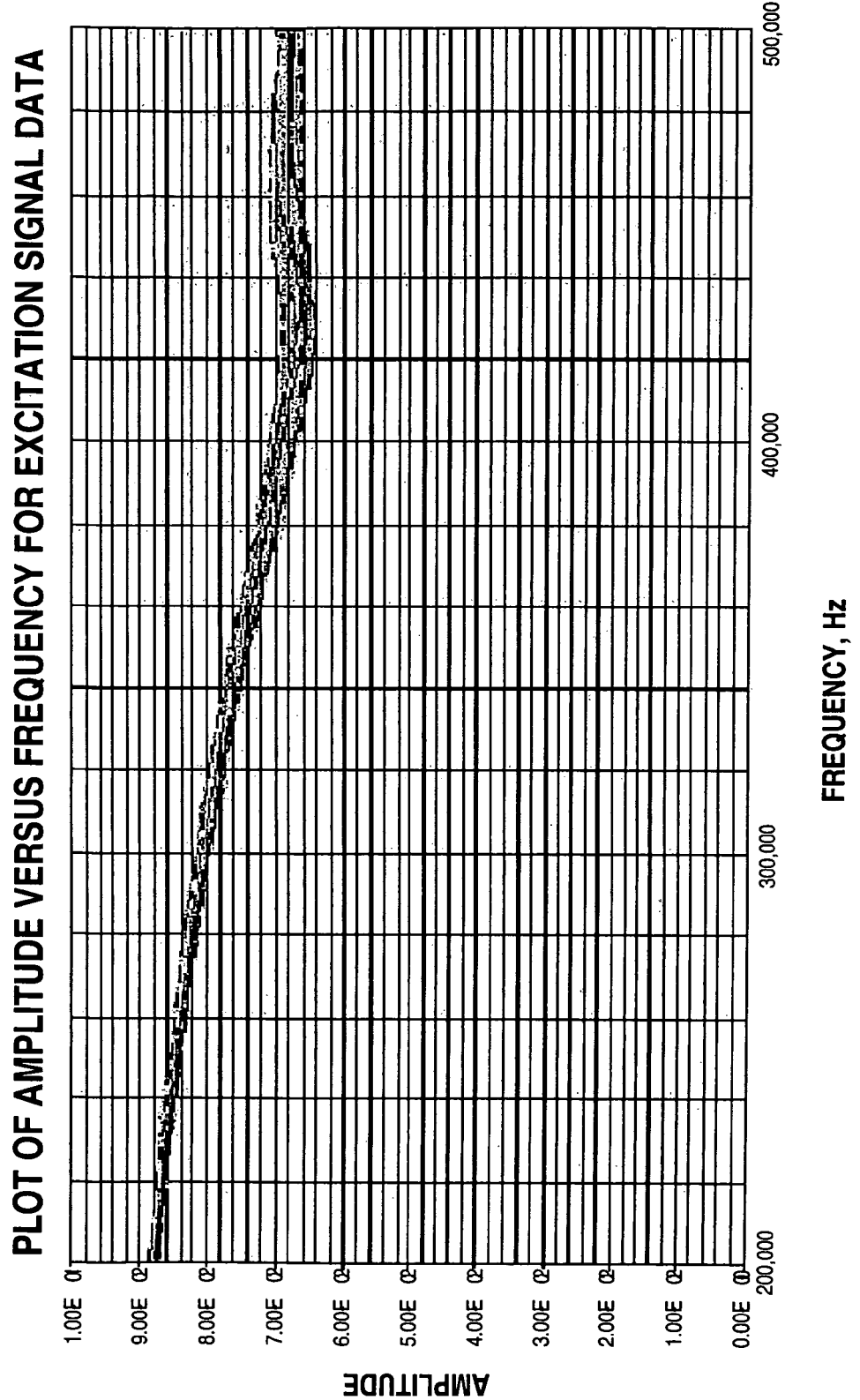
FIG. 3 represents a plot of the frequency versus amplitude transmitted by an individual transceiver shown in FIG. 1.
Figure 4:
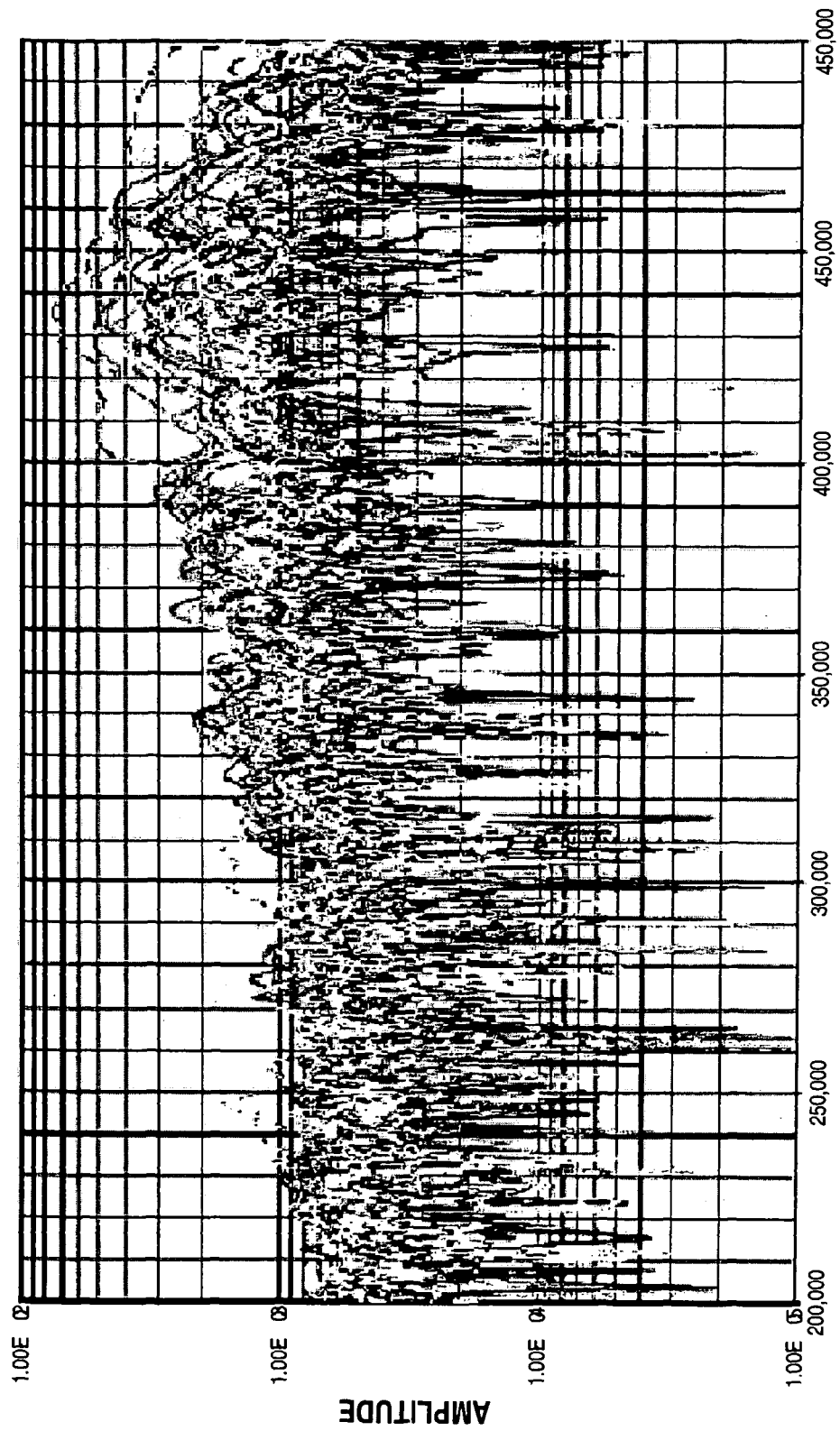
FIG. 4 represents a plot of the amplitude versus frequency received by an individual transceiver shown in FIG. 1.

FIGS. 3 and 4 represent a series of transmitted and received ultrasonic signals. As FIG. 3 shows, a series of rather broad band transmissions from the transceivers is produced. Each of the transceivers are configured to preferably transmit approximately the same signal. FIG. 4 represents an amplitude versus frequency plot of the signals received from each of the transmitting transceivers. Data acquisition of these received signals can be carried out using an IEEE PCI-GPIB data acquisition system which converts a personal computer into an instrumentation control and data acquisition system. FIG. 3 shows the source measurement for wave excitation from the sensors, while FIG. 4 shows the response measurement for the wave excitation from these sensors.

Figure 5A:
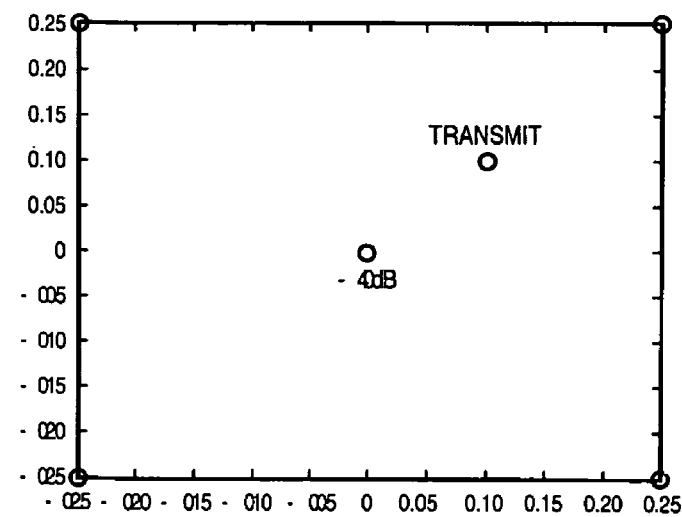
FIGS. 5A through 5C represent a modeling process used to determine the best sensor spacing to be used for the sensor array. Model predicted that the six inches sensor spacing produced the best resolution as shown in FIG. 5C.
Figure 5A:
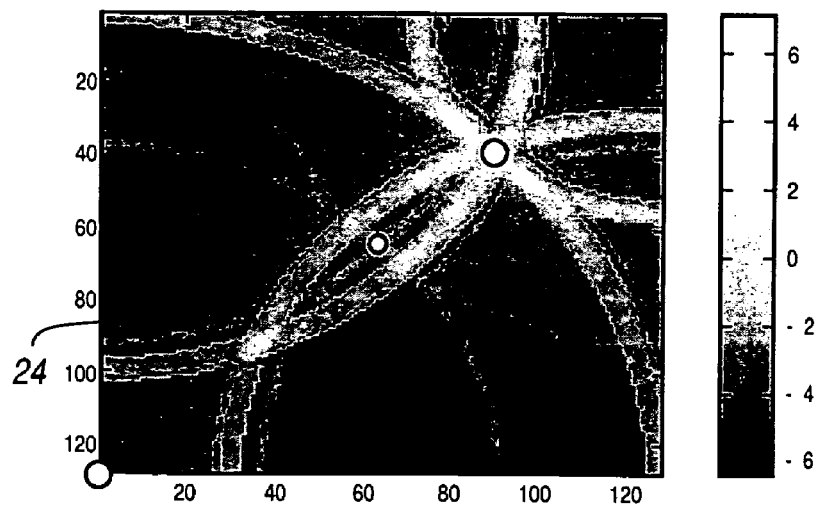
Figure 5A:
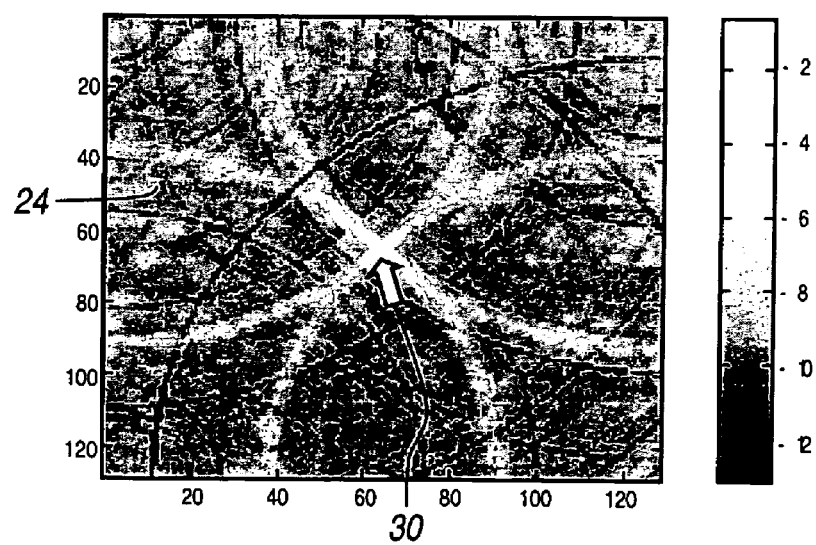
Figure 5B:
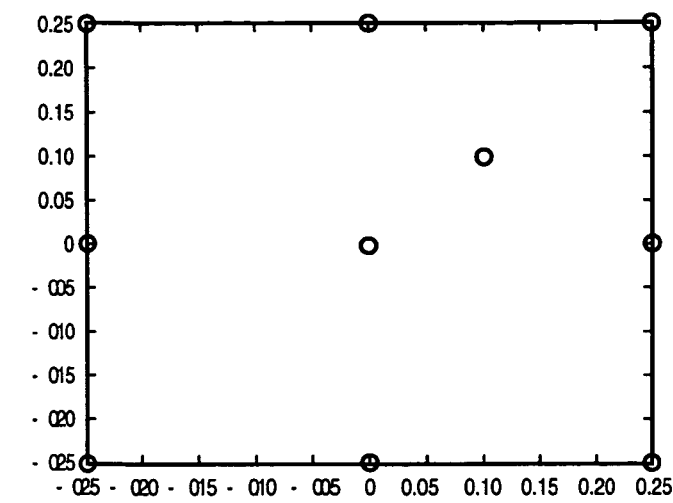
Figure 5B:
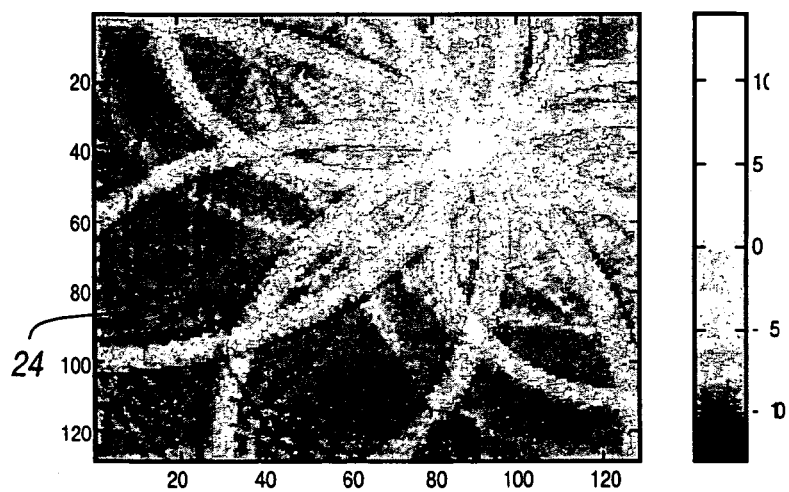
Figure 5B:
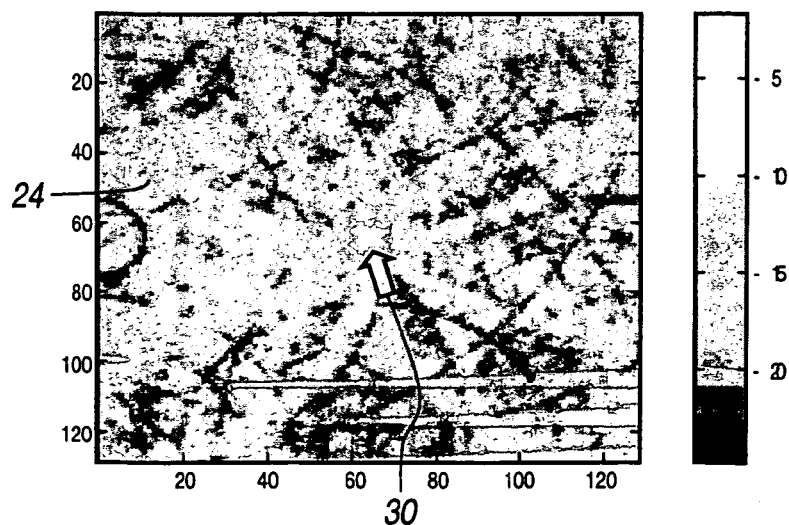
Figure 5C:
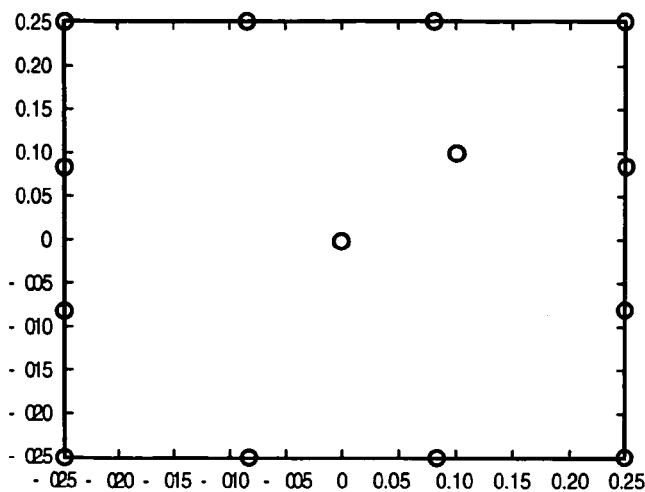
Figure 5C:
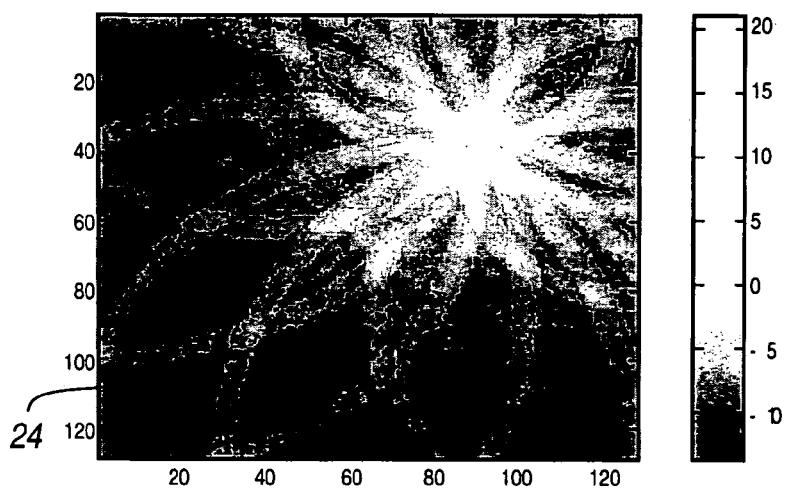
Figure 5C:
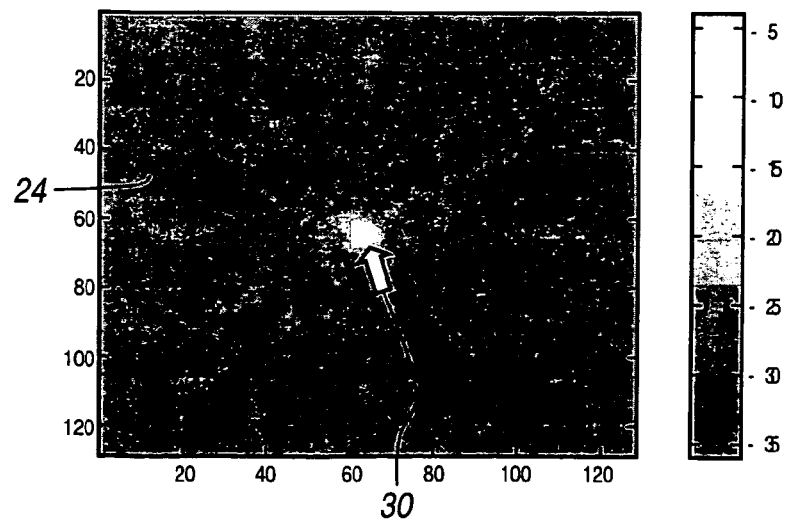

Preferably, at least nine piezoelectric transceivers 34 are coupled to the component 24. FIGS. 5A-5C represent the formation of an image using transceivers 34 disposed within the component 24 using sensors at various spacing. FIG. 5A represents an image formed using piezoelectric transceivers 34 positioned in an array with a 20 inch spacing. FIGS. 5B and 5C represent the images formed of a known defect using transceivers 34 spaced at 10 inches and 6 inches respectively. As can be seen, while the transceivers 34 spaced in a 20 inch array can detect a defect within a component 24, transceivers 34 spaced at 6 inches provide a easily distinguishable image of the defect within the area of the array coupled to the composite component 24. Shown is the image of a defect which is in the form of a lightened area on a standard computer monitor. This image can be optically evaluated, or evaluated using optical imaging procedures.

For Lamb wave imaging, the propagation speed of the Lamb wave is a function of the material properties as well as the thickness of the material. If a crack or a delamination or a change in material properties occurs, the speed of propagation will change. The basic principle of ART is based on imaging the region between transducers. The time-of-flight between the transducers are used to estimate the speed of propagation in many directions across the surface of the material. The square grid of unknown densities is to be solved by setting up algebraic equations for the unknowns in terms of the measured velocities. This approach can be used to localize the region where a change in material properties exists.

Figure 6:
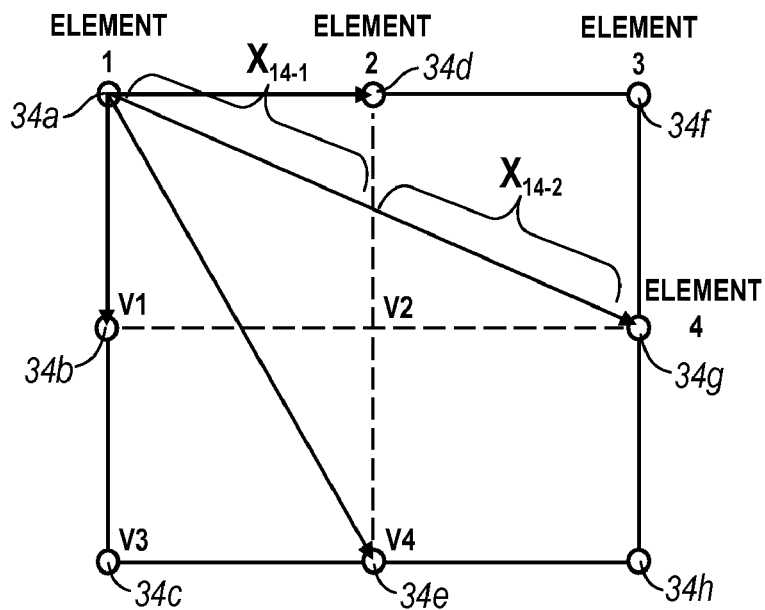
FIGS. 6 and 7 represent details of the functioning of the algebraic reconstruction tomography algorithm.

FIG. 6 represents a superimposed square grid on the image f(x,y); it is assumed that in each cell the function f(x,y) is constant. $F_j$ denotes this constant value in the $j^{th}$ cell and N is the total number of cells. A ray is defined as a "fat" line running through the f(x,y) plane. The $i^{th}$ ray has been shaded in FIG. 6. The ray sum is denoted by $p_i$. In most cases the ray width is approximately equal to the image cell width. Since the total time of flight along a ray path is equal to the sum of the individual times through the cells along the path, the relationship between the $f_i$'s and the $p_i$'s is $$\sum_{j=1}^{N} w_{ij} f_j = p_i, \quad i = 1, 2, \ldots, M$$

where M is the total number of rays in all projections. The factor $w_{ij}$ is equal to the fractional area of the $j^{th}$ image cell intercepted by the $i^{th}$ ray as shown for one of the cells in FIG. 6. Note that most of the $w_{ij}$'s are zero since only a small number of cells contribute to any given ray sum. This matrix equation is solved by conventional least squares matrix inversion methods or iterative solutions. W is known and p is measured.

$$Wf = p$$

With least squares solution:

$$f = (W^T W)^{-1} W^T p$$

Figure 7:
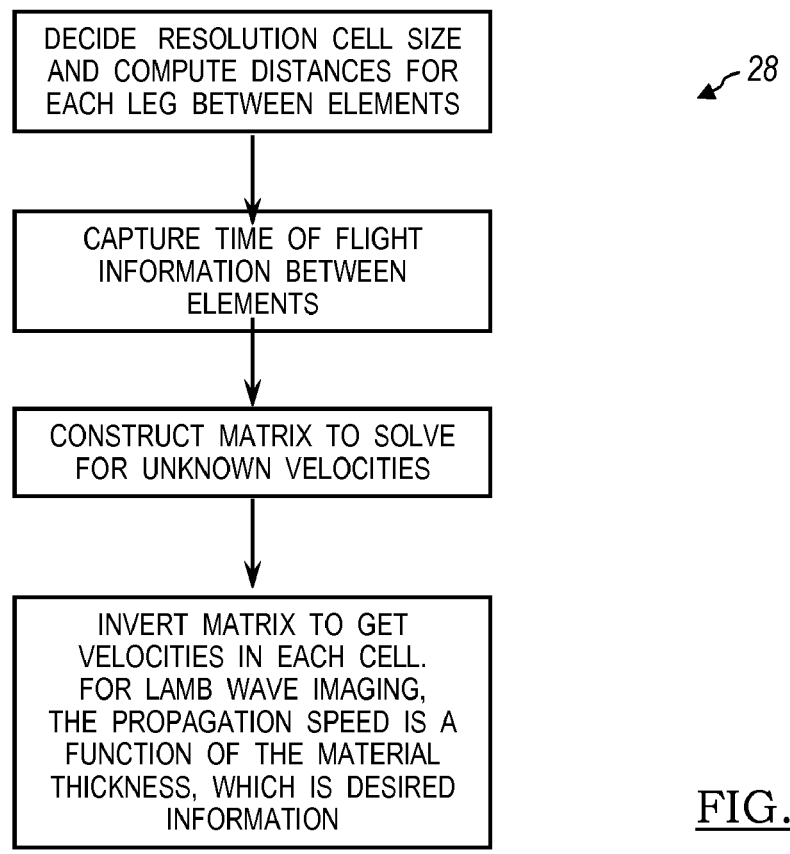

A summary of the Algebraic Reconstruction Tomography (ART) is shown and discussed in FIG. 7.

Figure 8:
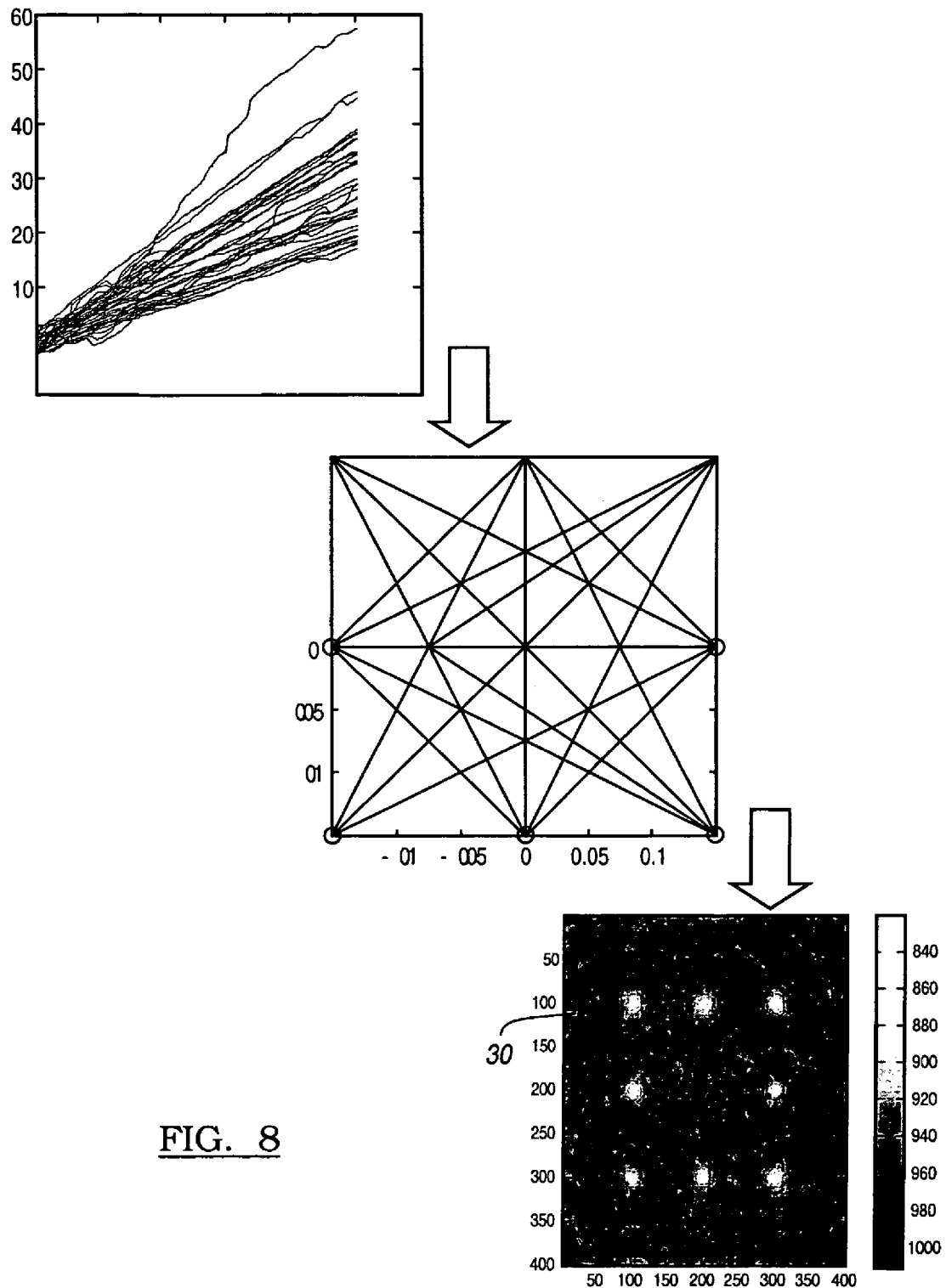
FIG. 8 represents a diagramic representation of the analysis performed by the algebraic reconstruction tomography algorithm to form the defect image.

FIG. 8 shows the data interpretation using the algebraic reconstruction tomography algorithm 28 to form images of the defect. Shown is the received signals which is processed using the algebraic reconstruction tomography algorithm 28 to form images of the defect. As previously mentioned, the resolution achievable by the algebraic reconstruction tomography algorithm 28 is a function of the number and location of the transceivers 34. The algebraic reconstruction tomography algorithm 28 is a ray-by-ray iterative technique that applies corrections as each ray is processed. The algebraic reconstruction tomography algorithm 28 assumes straight line rays and does not take into account scattered or ray bending. It is envisioned that correction for scattering from known structures such as fasteners, joints, and sensors can be carried out by deconvolving their contribution from the image data.

Figure 9:
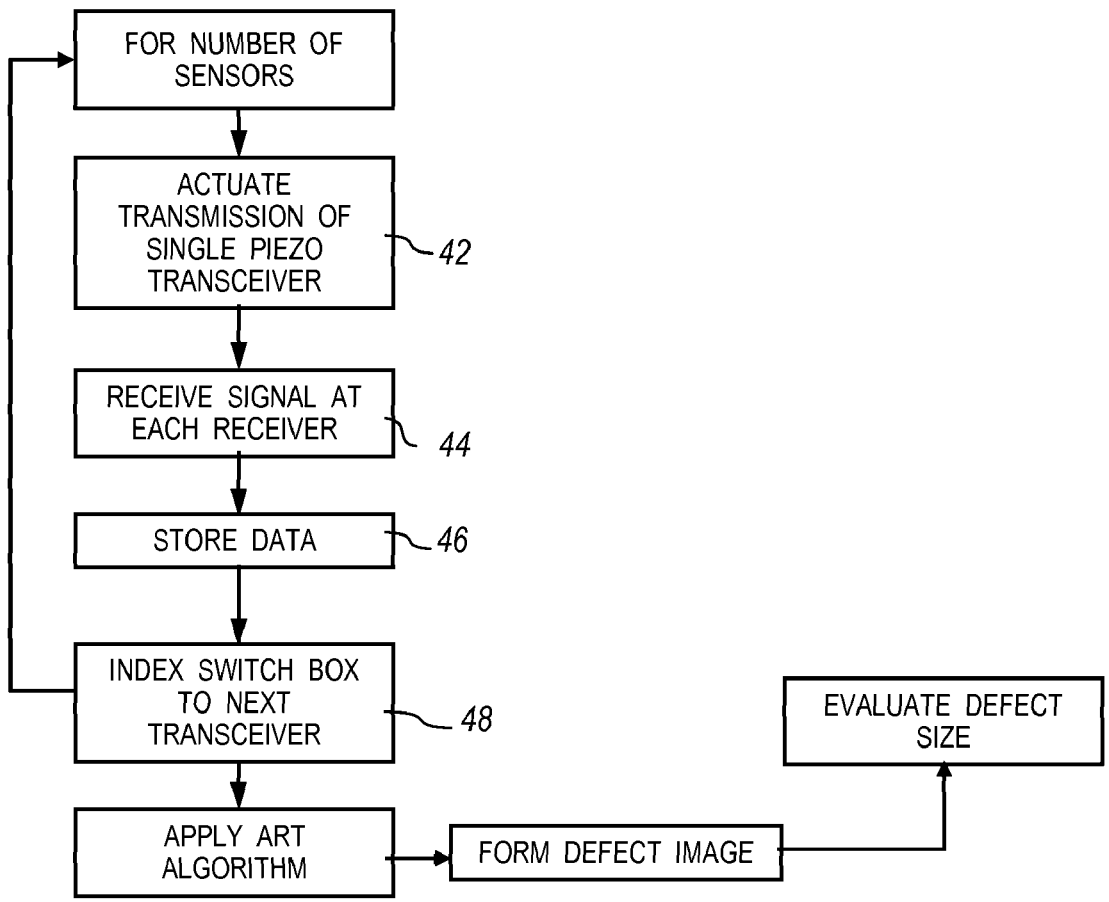
FIG. 9 represents a flow chart of the analysis of a component used in the mobile platform shown in FIG. 1.

FIG. 9 depicts a general functioning of the system 22. As shown after the image is calculated, an evaluation of the size and location of the defect is performed. It is envisioned that this analysis can be made or can, in real time, be made at a later date or time by an engineer. Specifically, the engineer can evaluate the location and size of the defect and determine if the defect is of sufficient size and location to adversely affect the functioning of the component. This analysis can either be qualitative or quantitative using available computer models such as Finite Element Analysis models.

By maintaining a database as to the current health status of a component or components in a system, an evaluation can be made as to whether a particular defect is growing over time. In this regard, images or data related to a defect can be stored and used to evaluate if there are changes within the component. Regular or event driven analysis would allow an evaluation of changes to the size of defects within the component. Further-more, an evaluation of individual components 24 can be made throughout the component's manufacturing and subsequent use. Prior to the curing of the composite component, piezoelectric transducers can be positioned within or on the surface of a composite laminate. Using the algebraic reconstruction tomography algorithm 28, defects such as voids, which can be resin rich areas or air bubbles or inclusions, can be found and evaluated prior to the curing of the component. If a defect of sufficient size in a critical location is discovered, the component can be reworked prior to curing.

After curing, the component can again be evaluated by the system to determine the location and size of manufacturing defects. Additionally, it is possible to evaluate general material properties of the component 24. At this point, electronic models such as Finite Element Analysis models can be used to evaluate whether a defect will inadvertently affect the performance of the component. Evaluation of the defects during the manufacturing process significantly reduces the cost of component manufacture as defects can be found early in the manufacturing process, thus reducing the number of additional manufacturing processes being performed on the unfinished component.

Additionally, component analysis can be conducted while the component is coupled to a complex structure or substructure associated with the mobile platform. In this regard, analysis of the component or components on the mobile platform can be conducted as a regular part of a mobile platform's normal maintenance requirements.

While various preferred embodiments have been described, those skilled in the art will recognize modifications or variations which might be made without departing from the inventive concept. For example, while it is envisioned the mobile platform of the present invention is a commercial fixed wing aircraft, the systems and methods described herein are equally applicable to other vehicles such as helicopters, military vehicles, launch vehicles, land vehicles such as automobiles or trucks, and sea based vehicles such as boats or submarines. Further, while the array of transceivers are shown being coupled to the processor using wires, it is envisioned that the transceivers can be wirelessly coupled to the processors using wireless systems such as those utilized IEEE 1451.3 compliant components or their equivalents. Additionally, while the array is shown as a planar 9×9 array of transceivers, it is envisioned that the array can consist of a 3-dimensional distribution of transceivers. The examples illustrate the invention and are not intended to limit it. Therefore, the description and claims should be interpreted liberally with only such limitation as is necessary in view of the pertinent prior art.

What is claimed is:

1. A system for evaluating the health of a component, the system comprising:
    a plurality of ultrasonic transmitters coupled to the component;
    a plurality of sensors coupled to the component, the sensors configured to receive signals transmitted through the component from the transmitters;
    a circuit configured to collect and store signals received by the sensors; and
    a processor configured to receive the stored signals and perform an algebraic reconstruction tomography algorithm wherein the algebraic reconstruction tomography algorithm functions to convert the received signals into an image of a defect within the component, wherein the component comprises a cured thermoplastic composite.

2. The system according to claim 1 wherein the ultrasonic transmitters comprise a plurality of ultrasonic transducers.

3. The system according to claim 2 wherein the ultrasonic transducers are disposed within the component.

4. The system according to claim 2 wherein the ultrasonic transducers are coupled to an exterior surface of the component.

5. The system according to claim 2 wherein the plurality of ultrasonic transducers are arranged in an array of generally equally spaced distances.

6. The system according to claim 1 wherein the plurality of sensors and plurality of transmitters is an array of piezoelectric transducers.

7. A system for evaluating the health of a component, the system comprising:
    a plurality of ultrasonic transmitters coupled to the component;
    a plurality of sensors coupled to the component, the sensors configured to receive signals transmitted through the component from the transmitters;
    a circuit configured to collect and store signals received by the sensors;
    a processor configured to receive the stored signals and perform an algebraic reconstruction tomography algorithm wherein the algebraic reconstruction tomography algorithm functions to convert the received signals into an image of a defect within the component; and
    a plurality of ultrasonic transducers, wherein the component comprises an uncured reinforced thermoplastic composite.

8. A system for analyzing the health of a reinforced composite structure, the system comprising:
    a plurality of transceivers coupled to the reinforced structure;
    a switching component coupled to the transceivers; and
    a processor coupled to the switching component, wherein the switching component is configured to recursively enable single transceivers to individually transmit a broad band vibrational pulse while the remaining transceivers are configured to receive the transmitted signal, said switching component further being configured to couple the transceivers to a processor, said processor being configured to receive the storage signals and process the signals to form an image of a defect within the reinforced composite structure, wherein the reinforced composite structure comprises a multi-layer cured thermoplastic composite.

9. The system according to claim 8 wherein the transceivers are configured to produce an ultrasonic vibrational pulse.

10. The system according to claim 8 wherein the transceivers are piezoelectric transceivers.

11. The system according to claim 8 wherein the processor is configured to run an algebraic reconstruction tomography algorithm.

12. The system according to claim 11 wherein the algorithm functions to convert the stored signals into the image.

13. A method of detecting a defect within a thermoplastic composite structure, the method comprising:
    operably coupling an array of ultrasonic transceivers to the thermoplastic structure, said array having a transmitting transceiver and a plurality of receiving transceivers;
    recursively enabling each transceiver of the array to individually transmit a broad band vibrational pulse and record the transmitted pulse using at least one of the non-transmitting transceivers;
    providing a processor configured to run an algebraic reconstruction tomography algorithm on the recorded pulse to form a first image of the defect within a component of the thermoplastic composite structure;

running the algebraic reconstruction tomography algorithm to form a first image;

storing data relating to the first image;

after a predetermined time, recursively enabling each transceiver of the array to individually transmit a second set of broadband vibrational pulses and recording the transmitted pulses using the non-transmitting transceivers;

running the algebraic reconstruction tomography algorithm to form a second image; and comparing data related to the first image to data related to the second image to evaluate a change in the defect.

14. The method according to claim 13 wherein the thermoplastic component is an uncured reinforced thermoplastic component.

15. The method according to claim 13 wherein the defect is a void.

16. The method according to claim 13 further including coupling the thermoplastic structure to a mobile platform.

17. The method according to claim 16 wherein running the algebraic reconstruction tomography algorithm is conducted after the component is coupled to the mobile platform.

18. The method according to claim 13 wherein the processor sets a counter to an initial condition for a counter less than a predetermined number of locations, and performs the following for the number of locations:

transmitting an ultrasonic signal from a single location, receiving a response signal at the remaining locations, and storing the received information in a plurality of memory locations; and incrementing the counter.

19. The method according to claim 13 further comprising evaluating the image of the defect and taking corrective action should the image of the defect meet a predetermined criterion.

\* \* \* \* \*